United States Patent [19]

Tsutsui et al.

[11] Patent Number: 4,672,045
[45] Date of Patent: Jun. 9, 1987

[54] METHOD FOR ASSAYING ANTIGEN-ANTIBODY REACTIONS AND REAGENT THEREOF

[75] Inventors: Satoshi Tsutsui, Yamato; Tadamitsu Sudo, Sagamihara; Michio Ito, Yokohama, all of Japan

[73] Assignee: Mitsubishi Chemical Industries Limited, Tokyo, Japan

[21] Appl. No.: 658,456

[22] Filed: Oct. 9, 1984

Related U.S. Application Data

[63] Continuation of Ser. No. 370,265, Apr. 20, 1982, abandoned.

[30] Foreign Application Priority Data

May 2, 1981 [JP] Japan .................................. 56-67333

[51] Int. Cl.$^4$ ................. G01N 33/536; G01N 33/543; G01N 33/546; G01N 33/574
[52] U.S. Cl. .................................... 436/518; 436/534; 436/536; 436/813; 436/826
[58] Field of Search ............... 436/501, 507, 500, 518, 436/517, 523, 528, 529, 530, 531, 532, 533, 534, 536, 808, 826, 520

[56] References Cited

U.S. PATENT DOCUMENTS

4,162,192 6/1979 Mizuno et al. ........................ 434/239
4,223,005 9/1980 Teodorescu et al. .................. 424/12

OTHER PUBLICATIONS

M. B. Gibbs in C. A. Williams et al. (EDS) *Methods in Immunology and Immunochemistry*, vol. IV, Academic Press, New York, 1977, pp. 4–9.
M. A. Sober (ed.) *CRC Handbook of Biochemistry*, The Chemical Rubber Co., Cleveland, 1968, p. C-36.
Bernfeld, Bio Abstracts, vol. 64, p. 1226 [#15413].
Methods in Enzymology, vol. 12, (Eds. Grossman and Moldare) Academic Press N.Y. (1968).
Polymers and Resins, Golding, Van Nostrand, (1959).
Juji, Japan, J. Exp. Med., vol. 39, No. 6, 1969, pp. 615–620.
The Merck Index, Merck & Co., 9th Ed., 1976, Ab. No. 4510

*Primary Examiner*—Esther M. Kepplinger
*Assistant Examiner*—David A. Saunders
*Attorney, Agent, or Firm*—Oblon, Fisher, Spivak, McClelland & Maier

[57] ABSTRACT

There are disclosed a method for assaying antigens or antibodies in the reaction medium, characterized in that a sample containing antigens or antibodies to be assayed is treated with a polyanion which is soluble in the reaction medium and thus treated sample is used for the antigen-antibody reaction; and a reagent for assaying an antigen-antibody reaction, which contains a polyanion and a reaction medium.

5 Claims, No Drawings

METHOD FOR ASSAYING ANTIGEN-ANTIBODY REACTIONS AND REAGENT THEREOF

This application is a continuation of application Ser. No. 370,265, filed Apr. 20, 1982, now abandoned.

BACKGROUND OF THE INVENTION

1. Field of the Invention

This invention relates to a method for antigen-antibody reactions and a reagent therefor.

2. Description of the Prior Art

At the present time, many in vivo reactions attract much attention in their relations to antigen-antibody reactions, particularly in the field of medicine and hygienic sciences and they are analyzed and investigated with the intention of promoting health conditions, treating diseases and the like. In addition, regarding in vitro reactions, immunochemical investigation is made intensely on the basis of samples which reflect in vivo conditions and a part thereof is already put to practical use in routine medical tests. Typical assay methods known as highly sensitive assay systems include radioimmunoassay (RIA), latex agglutination assay with near infrared turbidimetry (LPIA), enzyme immunoassay (EIA), fluoroimmunoassay, and nephelometry utilizing light scattering. Heretofore many immunological reactions have been conducted wherein antigens or antibodies in samples are detected with a reagent comprising, in addition to the liquid phase, the carrier matrix such as biological carriers, e.g., erythrocytes or bacteria and latex particles of synthetic organic polymer carriers, which can be sensitized with an appropriate antibody or antigen.

Immunological reactions show high specificity in that a reaction occurs strictly and selectively, which is one of their outstanding features, and they are assessed as an important medical test method.

On the other hand, body fluids which reflect activities of in vivo conditions have a wide variety of compositions and physical properties. On this account, many immunological reactions could not entirely be freed from non-specific reactions which can be said to be side reactions independent of the antigen-antibody reaction. As a countermeasure against such non-specific reactions, in many cases, such procedure as the addition of kaolin or similar adsorbent or extraction has been employed in order to remove or neutralize the relevant non-specific factors. Though part of such treatments are effective, it is necessary to make a detailed examination on each antigen-antibody reaction and they involve many difficulties in their practical use.

SUMMARY OF THE INVENTION

The inventors have made various investigations with the intention of eliminating the above-mentioned disadvantages of the prior art antigen-antibody reactions and found that in the assay of an antigen-antibody reaction, if the reaction is carried out with a sample which has been treated with a polyanion, both the recovery of the substance to be detected and the assay accuracy are improved to provide more accurate assay values of the antigen or antibody, thereby accomplishing this invention. Thus, the present invention provides a method for assaying an antigen-antibody reaction wherein an antigen or antibody to be assayed is reacted with the corresponding antibody or antigen in a reaction medium, characterized in that a sample containing the antigen or antibody to be assayed is treated with a polyanion which is soluble in the reaction medium and thus treated sample is used for the reaction; and a reagent for assaying an antigen-antibody reaction, which contains a polyanion and a reaction medium.

DETAILED DESCRIPTION OF THE PREFERRED EMBODIMENTS

Now the invention is described in detail.

The polyanions that can be used in the method of this invention are those substances comprising natural or synthetic polymers such as polysaccharides or polystyrene having therein plural anions such as sulfonyl anions or carboxyl anions, said materials being soluble in the reaction medium used in the antigen-antibody reaction.

Specific examples of these polyanions include dextran sulfate, heparin, polystyrene sulfonic acid, cellulose phthalate acetate, hyaluronic acid, chondroitin sulfate and the like.

According to the method of this invention, a sample containing the antigen or antibody to be assayed is treated with the polyanion and then subjected to the antigen-antibody reaction with the corresponding antibody or antigen in the reaction medium.

The treatment with the polyanion may be carried out (i) by carrying out the antigen-antibody reaction in the medium in which the polyanion has been included or (ii) by treating the sample with a solid or liquid phase containing the polyanion prior to the antigen-antibody reaction (in the latter case, the antigen- or antibody-containing sample thus treated may be subjected to the antigen-antibody reaction after the polyanion has been removed therefrom, but usually it is subjected to the reaction as it carries the polyanion).

The reaction media suitable for use in antigen-antibody reaction are aqueous media including, for example, water, a saline solution and buffer solutions, which may contain one or more additives selected from stabilizers, preservatives, chelating agents, surfactants, etc.

The buffer solution includes glycine buffers, phosphoric acid buffers, citric acid buffers, barbital buffers, borate buffers, Tris[tris(hydroxymethyl)aminomethane]-hydrochloric acid buffers, Tris-malate buffers, ammonia buffers and the like.

The stabilizers includes, for example, amino acids, polypeptides, proteins and the like which do not participate in the intended immunological reaction and they are usually present at concentrations of 0.001% to 1%, preferably 0.05% to 0.6%.

Preferred examples of the preservatives include sodium azide and merthiolate.

Preferred examples of the chelating agents include ethylenediaminetetraacetic acid, nitrilotriacetic acid, cyclohexanediaminetetraacetic acid and the like.

As the surfactant, nonionic surfactants are generally preferred.

The pH of the reaction medium should be in the ordinary pH range applicable to antigen-antibody reactions and usually a pH of about 5 to 10 is employed.

The concentration of the polyanion in the reaction medium is usually not greater than 5% by weight, preferably from 0.001 to 0.5% by weight.

A higher concentration may cause the reaction to become unstable in the case of some assay systems. But a lower concentration, the inhibitory effect against the so-called non-specific reactions which interfere with the assay and make it impossible to obtain accurate assay values is decreased because of an increased inhibitory effect caused by factors in the serum sample other than the reaction with the corresponding antigen, resulting in a decreased accuracy of the assay.

The antigens which serve as a substance to be assayed and a reactant include various ones such as, for example, proteins, polypetides, steroids, polysaccharides, lipids, pollen, dust, and haptens. The antibodies include, for example, those proteins which are the antibodies against the above-mentioned antigens.

The assay of an antigen-antibody reaction according to this invention is applicable to any assay systems well known in the art. Thus, it can be applied either to the so-called solution systems wherein both the substance to be assayed and the reactant are soluble in the reaction medium, or to the so-called carrier systems wherein the reactant is supported on a particulate carrier which is substantially insoluble in the reaction medium, that is to say, the particulate carrier is sensitized with the reactant. Specific examples of the antigen-antibody reactions that can be assayed according to the method of this invention include those reactions occurring in radioimmunoassay, latex agglutination with near infrared turbidimetry, enzyme immunoassay, fluoroimmunoassay, immunonephelometry utilizing light scattering, erythrocyte agglutination, latex agglutination and the like. Particularly the method of this invention is preferably applied to such assay system as latex agglutination with near infrared turbidimetry that can utilize, for example, a reversed passive agglutination.

In accordance with the method of this invention, non-specific reactions which may occur in antigen-antibody reactions can be prevented and more accurate assay values can be obtained.

Having generally described the invention, a more complete understanding can be obtained by reference to certain specific examples, which are included for purposes of illustration only and are not intended to be limiting unless otherwise specified.

The percentages in the examples are by weight.

EXAMPLE 1

This example illustrates latex agglutination with near infrared turbidimetry.

To 50 μl of serum from a normal human containing no greater than 2 ng/ml of $\alpha_1$-fetoprotein (AFP) were added 50 μl of a solution containing 1 μg/ml of AFP and then 100 μl of bovine serum albumin saline containing dextran sulfate to make a test solution. To 50 μl of the test solution were added 50 μl of a latex reagent sensitized with anti-AFP antibody and 200 μl of a buffer solution and the change of turbidity in a near infrared ray at 940 nm was measured under stirring. The assay value of the sample was read on a standard curve and the recovery was calculated. The results are shown in Table 1 below as compared with those of a polyanion-free reaction system as a control.

As is apparent from Table 1, a significant improvement in recovery ($P<0.01$) was attained by addition of dextran sulfate (at a final concentration of 0.1%) and the coefficient of variation (CV) was also greatly improved. The recovery in each run is the relative value on the recovery obtained with normal pooled serum of ten clear, turbidity-free samples taken as 100.

EXAMPLE 2

The procedure of Example 1 was repeated except that the polyanion was polystyrene sulfonic acid at a final concentration of 0.2%. The results are also included in Table 1, from which it can be seen that improvement in coefficient of variation was obtained.

EXAMPLE 3

The procedure of Example 1 was repeated except that heparin is used as a polyanion at a final concentration of 0.1%. As shown in Table 1, improvement in recovery was noted.

EXAMPLE 4

The procedure of Example 1 was repeated except that cellulose phthalate acetate was used as a polyanion at a final concentration of 0.1%. As is shown in Table 1, the recovery was improved.

TABLE 1

| | Sample | | Recovery (%) | | | | |
|---|---|---|---|---|---|---|---|
| Run No. | Hemolysis | Turbidity | Control No polyanion | Example 1 Dextran sulfate | Example 2 Polystyrene sulfonic acid | Example 3 Heparin | Example 4 Cellulose phthalate acetate |
| 1 | − | +++ | 93.7 | 101.4 | 93.9 | 96.2 | 98.3 |
| 2 | − | +++ | 86.8 | 88.8 | 88.2 | 88.9 | 88.9 |
| 3 | − | +++ | 83.8 | 105.8 | 80.2 | 87.2 | 82.9 |
| 4 | ++ | +++ | 88.0 | 96.5 | 90.0 | 92.2 | 93.2 |
| 5 | − | +++ | 76.7 | 86.6 | 80.3 | 82.3 | 85.2 |
| 6 | − | + | 84.6 | 98.1 | 85.2 | 87.8 | 91.2 |
| 7 | − | + | 90.7 | 103.3 | 93.4 | 93.5 | 98.5 |
| 8 | − | + | 85.9 | 103.0 | 86.8 | 85.9 | 91.7 |
| 9 | − | + | 72.9 | 96.2 | 85.0 | 82.4 | 91.7 |
| 10 | − | + | 100.6 | 100.6 | 100.0 | 99.8 | 101.7 |
| 11 | − | + | 105.1 | 100.4 | 89.9 | 100.2 | 111.2 |
| 12 | ++ | + | 92.7 | 101.0 | 94.3 | 102.0 | 98.4 |
| 13 | + | + | 96.5 | 99.1 | 97.8 | 100.0 | 101.2 |
| 14 | + | + | 92.4 | 97.5 | 95.2 | 99.0 | 101.2 |
| 15 | − | + | 100.0 | 100.2 | 97.5 | 102.0 | 101.5 |
| 16 | + | + | 79.6 | 93.1 | 80.4 | 85.0 | 88.4 |
| 17 | − | − | 95.6 | 100.1 | 95.5 | 99.4 | 100.9 |
| 18 | + | − | 81.1 | 93.2 | 87.5 | 85.5 | 93.5 |
| 19 | +++ | − | 82.6 | 85.5 | 83.7 | 87.0 | 86.0 |
| 20 | − | − | 92.0 | 105.1 | 97.2 | 102.0 | 98.0 |
| Average | | | 89.07 | 97.78 | 90.1 | 92.92 | 95.18 |
| Standard deviation | | | ±8.39 | ±5.76 | ±6.33 | ±7.21 | ±7.07 |

TABLE 1-continued

| | Sample | | Recovery (%) | | | | |
|---|---|---|---|---|---|---|---|
| Run No. | Hemo-lysis | Turbi-dity | Control No polyanion | Example 1 Dextran sulfate | Example 2 Polystyrene sulfonic acid | Example 3 Heparin | Example 4 Cellulose phthalate acetate |
| | CV (%) | | 9.42 | 5.89 | 7.02 | 7.76 | 7.43 |

EXAMPLE 5

This example illustrates the effect of addition of dextran sulfate on erythrocyte agglutination, which may be accompanied by a pseudo-reaction with some samples, resulting in misreading.

An AFP-containing sample was diluted 20 times with a solution of dextran sulfate in a phosphate buffer (pH 6.4) which was so prepared that the final concentration of dextran sulfate was 0.001% and 100 μl of the diluted sample was added to a suspension of sheep erythrocytes sensitized with anti-AFP antibody. The mixture was allowed to stand for 2 hours. Those samples containing no greater than 50 mg/ml of AFP showed ring-shaped agglutination, while those containing no less than 100 ng/ml of AFP showed either apparently larger ring-shaped or mat-like agglutination. When the same experiment was made with samples of known concentrations, less pseudo-reactions occurred even in the case of highly turbid samples facilitating the judgment.

Having now fully described this invention, it will be apparent to one of ordinary skill in the art that many changes and modifications can be made thereto without departing from the spirit or scope of the invention as set forth herein.

What is claimed as new and intended to be covered by Letters Patent is:

1. A method for assaying an antigen-antibody reaction in an aqueous medium, which comprises:
    (a) treating a sample containing an antigen or antibody to be assayed with from 0.001 to 5.0 percent by weight of a water soluble polymeric polyanion selected from the group consisting of cellulose phthalate acetate, hyaluronic acid, dextran sulfate, heparin, polystyrene sulfonic acid and chondroitin sulfate which is soluble in the aqueous reaction medium;
    (b) reacting the treated sample containing the polyanion at a concentration of from 0.001 to 5% with a complimentary antibody or antigen; and
    (c) assaying the reaction.
2. The method of claim 1 wherein said polyanion ranges from 0.001 to 0.5% by weight of the reaction medium.
3. The method as defined in claim 1 wherein the polyanion is dextran sulfate.
4. The method as defined in claim 1 wherein the antigen-antibody reaction is agglutination.
5. The method as defined in claim 4 wherein the agglutination is reverse passive agglutination.

* * * * *